(12) United States Patent
Ross

(10) Patent No.: US 9,782,223 B2
(45) Date of Patent: Oct. 10, 2017

(54) SURGICAL TRAJECTORY ALIGNMENT DEVICE

(71) Applicant: Christopher Daniel Ross, Davie, FL (US)

(72) Inventor: Christopher Daniel Ross, Davie, FL (US)

( * ) Notice: Subject to any disclaimer, the term of this patent is extended or adjusted under 35 U.S.C. 154(b) by 491 days.

(21) Appl. No.: 14/312,322

(22) Filed: Jun. 23, 2014

(65) Prior Publication Data

US 2014/0378997 A1 Dec. 25, 2014

Related U.S. Application Data

(60) Provisional application No. 61/838,021, filed on Jun. 21, 2013.

(51) Int. Cl.
*A61B 19/00* (2006.01)
*A61B 90/11* (2016.01)
*A61B 17/34* (2006.01)

(52) U.S. Cl.
CPC ............ *A61B 19/201* (2013.01); *A61B 90/11* (2016.02); *A61B 2017/3409* (2013.01)

(58) Field of Classification Search
USPC .................................................... 606/30, 86
See application file for complete search history.

(56) References Cited

U.S. PATENT DOCUMENTS

| | | | |
|---|---|---|---|
| 2003/0130648 A1* | 7/2003 | Jensen | A61B 34/76 606/1 |
| 2006/0089626 A1* | 4/2006 | Vlegele | A61B 17/3403 606/1 |
| 2011/0276100 A1* | 11/2011 | Birkbeck | A61F 2/4609 606/86 R |

* cited by examiner

*Primary Examiner* — Nicole F Johnson
(74) *Attorney, Agent, or Firm* — The Concept Law Group, P.A.; Scott D. Smiley

(57) ABSTRACT

A surgical trajectory alignment device is disclosed, including an alignment trajectory guide holding portion shaped to receive and secure an alignment trajectory guide along a longitudinal patient entry axis, the longitudinal patient entry axis falling within a plane. The surgical trajectory alignment device further includes a first alignment trajectory guide holding portion activator operable to rotate an alignment trajectory guide secured by an alignment arm holding portion within the plane; and a second alignment trajectory guide holding portion activator operable to translate an alignment trajectory guide secured by the alignment arm holding portion in a direction away from the plane.

19 Claims, 16 Drawing Sheets

SURGICAL TRAJECTORY ALIGNMENT DEVICE

CROSS-REFERENCE TO RELATED APPLICATION

This application claims priority to U.S. Provisional Patent Application No. 61/838,021 filed on Jun. 21, 2013, the entirety of which is incorporated by reference.

FIELD OF THE INVENTION

The present invention relates generally to an alignment device, and, more particularly, relates to a surgical trajectory alignment device for performing trajectory alignment of a medical device during a medical procedure.

BACKGROUND OF THE INVENTION

Medical procedures, such as deep brain stimulation, deep brain infusion, and biopsy procedures, often require mapping the trajectory of a medical device to reach a target point within a patient during the medical procedure. The target point may be, for example, a brain tumor that must be removed by the physician during surgery. A known system for performing trajectory alignment involves the use of a Navigus trajectory guide. A fluid filled stem is placed within the Navigus trajectory guide to monitor the trajectory using images displayed on a medical imaging viewing system, such as a Magnetic Resonance Imaging (MRI) viewing system connected to an MRI scanner. The Navigus trajectory guide is placed over the burr hole and is secured to the skull with three bone screws. Normally, a physician, located at the MRI scanner, manually adjusts the Navigus trajectory guide secured to the patient at the MRI scanner, while using instructions provided by the medical imaging technologist located at the MRI viewing system, to align the medical device with the trajectory defined by the target point. Once the adjustment is made, an additional MRI scan is performed to view the results of the adjustment. This process may take several attempts before the physician is able to appropriately align the medical device to reach the target point within the patient. Consequently, this process is time consuming because the physician performs the alignment based on the guidance of the medical technologist, each of whom are typically located in a separate room. This process is also dangerous for the patient due to possible negative long term effects of prolonged exposure to anesthesia.

A known system of performing trajectory alignment is stereotaxic targeting. With this system, the target point is determined using preoperative MRI images. From the images, the burr hole location is determined to accommodate insertion of the medical device along a generally vertical axis. Preferably, the burr hole is placed over non-essential brain tissue. The medical device is inserted through the burr hole using a micromanipulator on a stereotaxic frame. Unfortunately, this system does not accommodate off axis trajectories for placement of the medical device in irregularly shaped targets, such as the putamen, located at the base of the forebrain. An additional problem presented by this method is that the trajectory is determined based upon preoperative images, rather that images produced in real time.

Another known system, the arc-phantom system (a type of sterotaxic targeting) also involves several lengthy steps in performing the trajectory alignment. Using the arc-phantom system, initially, an aiming bow is attached to a head ring that is fixed to the patient's skull. The aiming bow can be transferred to a similar ring that contains a replicated target. The aiming bow is then adjusted to reach the desired replicated target. Once the replicated target is reached with the aiming bow, the system is placed back on the patient's skull.

Additional problems presented by many known trajectory alignment systems are difficult assembly and difficult adjustment of the trajectory alignment systems. Many of the known trajectory alignment systems involve several components that must be assembled prior to using the system. Likewise, many of the known targeting systems involve several steps and manipulation of components in order to perform the trajectory alignment of the medical device to reach the target point within the patient.

Therefore, a need exists to overcome the problems with the prior art as discussed above.

SUMMARY OF THE INVENTION

The invention provides a surgical trajectory alignment device that overcomes the hereinafore-mentioned disadvantages of the heretofore-known devices of this general type, and that provides a surgical trajectory alignment device for performing trajectory alignment of a medical device during a medical procedure.

With the foregoing and other objects in view, there is provided, in accordance with the invention, a surgical trajectory alignment device including an alignment trajectory guide holding portion shaped to receive and secure an alignment trajectory guide along a longitudinal patient entry axis. The longitudinal patient entry axis falls within a plane. A first alignment trajectory guide holding portion activator is operable to rotate an alignment trajectory guide secured by an alignment arm holding portion within the plane. A second alignment trajectory guide holding portion activator is operable to translate an alignment trajectory guide secured by the alignment arm holding portion in a direction away from the plane.

In accordance with a further feature of the present invention, an alignment arm supports the alignment trajectory guide holding portion.

In accordance with an additional feature of the present invention, the first alignment trajectory guide holding portion activator and the second alignment trajectory guide holding portion activator are coupled to and manipulate the alignment arm.

In accordance with another feature of the present invention, the alignment arm defines an arm axis, and the direction away from the plane is a longitudinal direction of the arm axis.

In accordance with another feature, an embodiment of the present invention includes a surgical trajectory alignment device for guiding a medical device to a target area within a subject through an entry point on the subject. The surgical trajectory alignment device includes a base couplable to a subject, a medical device extending through the base and into the subject and an arm coupled to the base. The arm includes a receiving portion shaped to receive and secure at least a portion of the medical device. The arm is operably configured to rotate the medical device through the base and upon an alignment axis for aligning the medical device with a target area within the subject. The arm is also operably configured to translate the medical device through the base and along the axis for aligning the medical device with the target area within the subject.

In accordance with another feature of the present invention, the base defines an opening operably configured to receive an alignment trajectory guide holding portion shaped to receive and secure an alignment trajectory guide.

In accordance with another feature of the present invention, a rotation device is coupled to the arm and operable to rotate the arm about the alignment axis. A translation device coupled to the arm and operable to translate the arm along a linear path from a first point to a second point along the alignment axis.

In accordance with yet another feature of the present invention a first cable couples the rotation device to a first actuator located at a remote control station outside a magnetic field of a magnetic resonance imaging device.

In accordance with an additional feature of the present invention, at least one gear is coupled to the rotation device.

In accordance with another feature of the present invention, the rotation device and the translation device are on a single side of the base.

In accordance with another feature of the present invention, the arm is configured to align the medical device to the target area within the subject by one of a rotational and a translational motion.

In accordance with an additional feature of the present invention, the arm includes a first end and a second end, opposite the first end. The arm includes at least one finger at the first end. The finger forms an opening for receiving the medical device therethrough. The finger is operably configured to receive a portion of a guide tube and the guide tube is configured to receive the medical device. The arm is coupled to a rotation device at the second end.

In accordance with an additional feature of the present invention, the arm is disposed in a horizontal position, substantially perpendicular to the entry point defined by the medical device.

In accordance with an additional feature of the present invention, the base and the arm are of at least one of a plastic and a ceramic material.

In accordance with another feature of the present invention, an embodiment of the present invention includes a surgical trajectory alignment device for guiding a medical device to a target area within a subject through an entry point on the subject. The surgical trajectory alignment device includes a body having a base having a portion couplable to a subject, a first arm, and a second arm. The first arm is coupled to the base and includes a receiving end defining a first opening for receiving at least a portion of the medical device therethrough for insertion of the medical device through an entry point on the subject. The first arm is operably configured to rotate about a first axis substantially parallel to a longitudinal length of the first arm for aligning an entry axis defined by the medical device to a target area with the subject. The second arm is coupled to the base and includes a receiving end defining a second opening for receiving at least a portion of the medical device therethrough for insertion of the medical device through the entry point on the subject. The second arm is operably configured to rotate about a second axis for aligning the entry axis to the target area with the subject. The second axis is substantially parallel to a longitudinal length of the second arm, and substantially perpendicular to the first axis. The receiving end of the first arm overlaps the receiving end of the second arm for jointly guiding movement of the medical device therein.

In accordance with another feature of the present invention, the body further includes a first rotation device having a first end and a second end. The first end is coupled to the first arm, and the second end is coupled to an actuator at a remote control station in close proximity to a medical imaging display. The body further includes a second rotation device having a first end and a second end. The first end is coupled to the second arm, and the second end is coupled to the actuator at a remote control station in close proximity to a medical imaging display.

In accordance with another feature of the present invention, the first arm and the second arm are operably configured to align the entry axis to the target area by rotational movements.

In accordance with yet another feature of the present invention, the body is comprised of a non-metallic material, the non-metallic material compatible with a Magnetic Resonance Imaging (MRI) scanner.

In accordance with an additional feature of the present invention, the base defines a third opening operably configured to receive a base member of a Navigus trajectory guide. The opening is disposed below an intersection area. The intersection area is defined by the area where the receiving end of the first arm overlaps the receiving end of the second arm.

In accordance with another feature of the present invention, the base defines a third opening for receiving a base member coupled to a locking ring. The locking ring includes a diameter less than a diameter of the base member. The locking ring is sized to be received through a top opening of the base member and frictionally retained within the base member.

Although the invention is illustrated and described herein as embodied in a surgical trajectory alignment device, it is nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of an axis.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
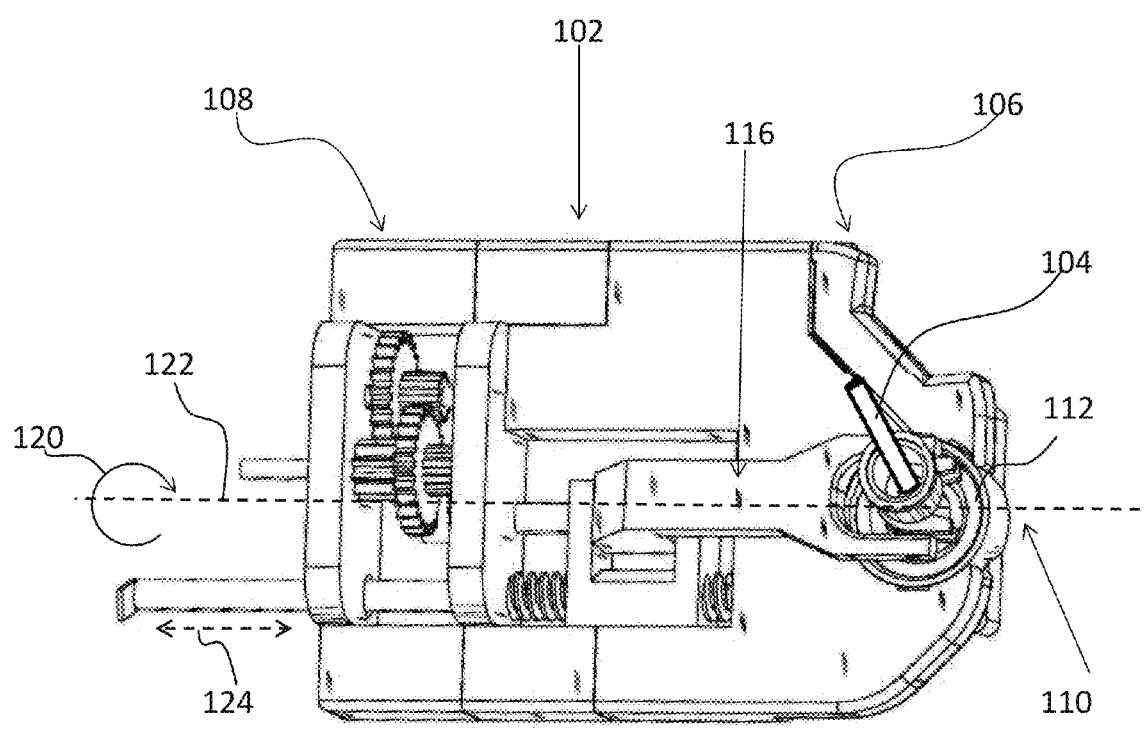
FIG. 1 is a downward-looking perspective view of an exemplary embodiment of a surgical trajectory alignment device in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient surgical targeting alignment device for aligning an instrument with a designated area in a precise and rapid manner. Embodiments of the invention provide a surgical targeting alignment device that is simple to assemble, and which is operable for guiding a medical device to a target area within a subject through an entry point on the subject, during various medical procedures. In addition, embodiments of the invention provide a surgical targeting alignment device that is of a material does not affect magnetic resonance imaging (MRI) readings or procedures.

Referring now to FIG. 1, one embodiment of the present invention is shown in a downward-looking perspective view. FIG. 1 shows several advantageous features of the present invention, but, as will be described below, the invention can be provided in several shapes, sizes, combinations of features and components, and varying numbers and functions of the components. The surgical trajectory alignment device 100 is shown having a base 102 including a first end 106 and a second end 108, opposite the first end 106.

Figure 2:
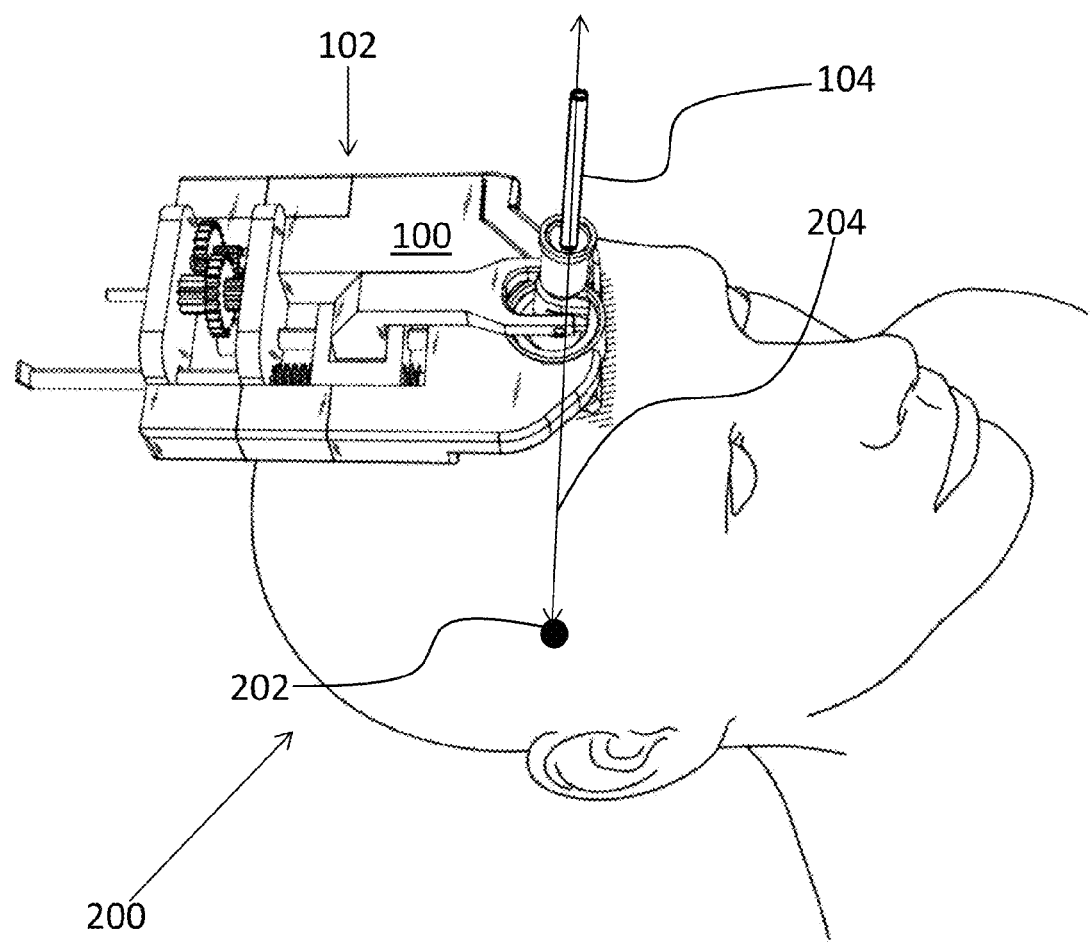
FIG. 2 is a downward-looking perspective view of the surgical trajectory alignment device of FIG. 1, showing the surgical trajectory alignment device coupled to a subject.

Referring now primarily to FIG. 2, the base 102 is a frame that is removably couplable to a subject 200. In use, the base 102 is coupled to the subject 200 to align an instrument, such as a medical device 104, along an entry axis 204 to reach a target area 202 within the subject 200. The "entry axis" is defined herein as an axis of a trajectory defined by the target area 202 within the subject 200 and an entry point on the subject 200, through which the medical device 104 must enter the subject 200 to reach the target area 202. The "target area" is defined herein as an area, a point, or a region within the subject 200 that the surgeon desires the medical device 104 to reach for operating thereon, such as, for example, a brain tumor.

The medical device 104 can be seen extending through the base 102 and into the subject 200. The type of medical device 104 varies depending upon the type of procedure for which the surgical trajectory alignment device 100 is being used. For example, the medical device 104 may be a catheter, with a portion capable of delivering drugs to the subject 200. In another example, for use during needle biopsy, the medical device 104 may be a needle that is inserted into the subject 200 to extract a portion of a tumor or tissue.

Figure 14:
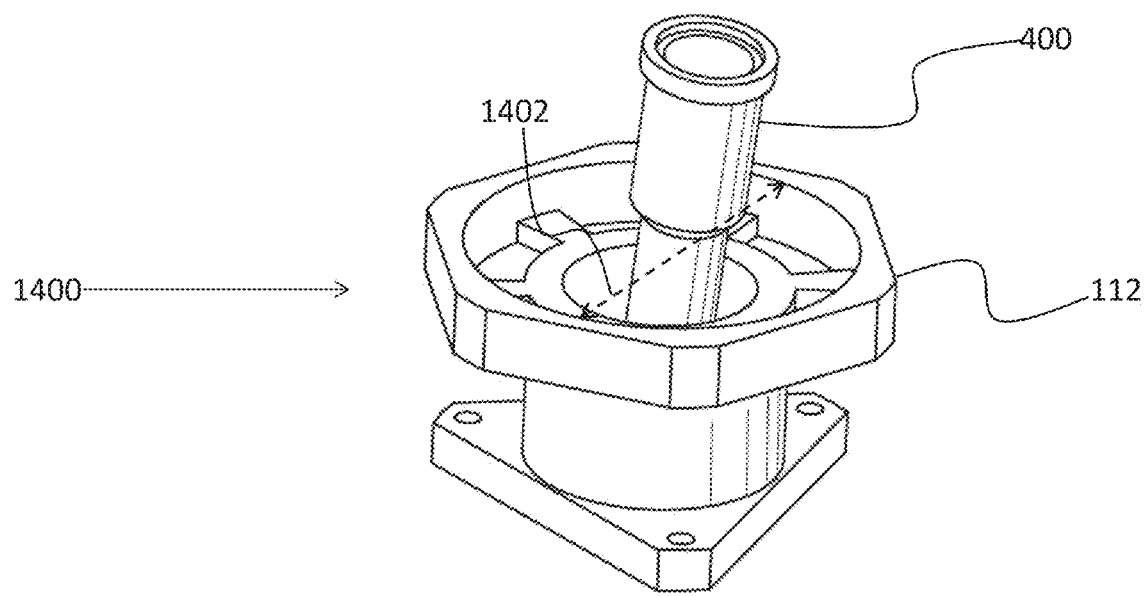
FIG. 14 is an enlarged, perspective view of the locking ring as shown by the prior art.
Figure 15:
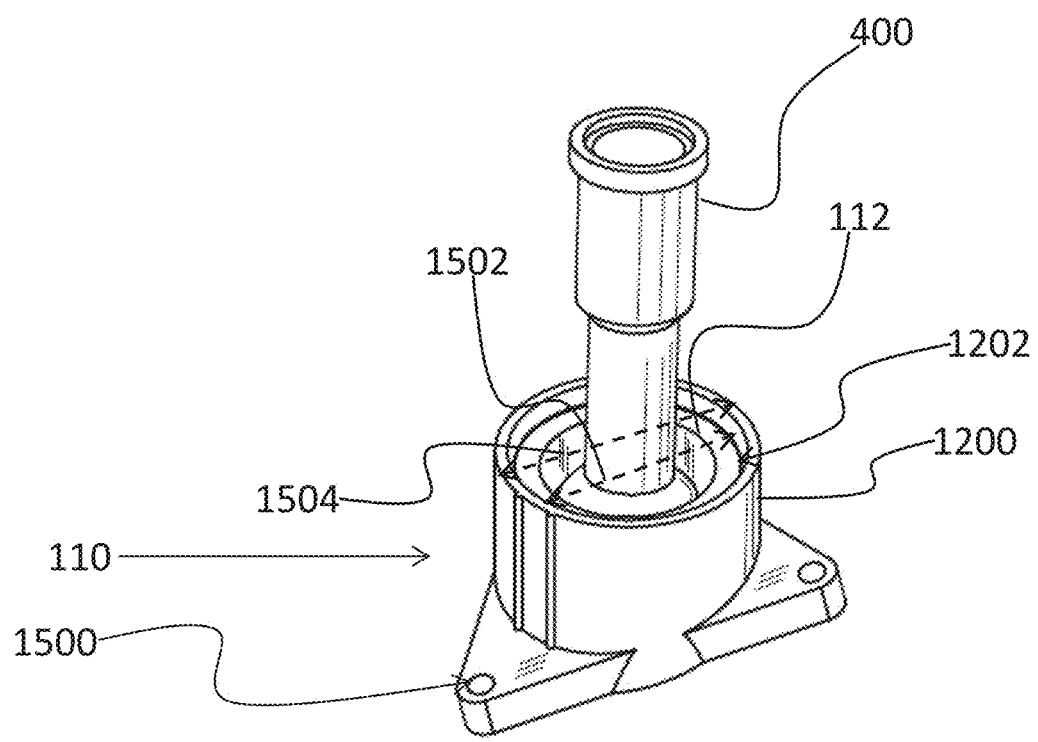
FIG. 15 is an enlarged, perspective view of an embodiment of the locking ring, showing the locking ring having a diameter less than a diameter of the base member, in accordance with the present invention.

Referring back to FIG. 1, the surgical trajectory alignment device 100 is shown in an assembled mode. The surgical trajectory alignment device 100 has an alignment trajectory guide holding portion 110 removably coupled to the base 102 at the first end 106. In an embodiment, the alignment trajectory guide holding portion 110 includes a locking device from the Navigus trajectory guide 1400 as manufactured by Medtronic® (see FIG. 14). FIG. 1 illustrates the alignment trajectory guide holding portion 110 including a locking ring 112. The alignment trajectory guide holding portion 110 is shown coupled to the base 102. In embodiments, the alignment trajectory guide holding portion 110 may be coupled to the base by a bolt, lug, nail, tab, male-female fasteners, or other similar fasteners. The alignment trajectory guide holding portion 110 is a platform secured to the subject 200 and which is operable for insertion of at least a portion of the medical device 104 therethrough. The alignment trajectory guide holding portion 110 includes multiple embodiments, as shown in FIG. 14 and FIG. 15, and discussed in more detail below. The embodiments shown in FIG. 14 and FIG. 15 are not exclusive embodiments, rather, the alignment trajectory guide holding portion 110 may include other embodiments, as well.

Figure 4:
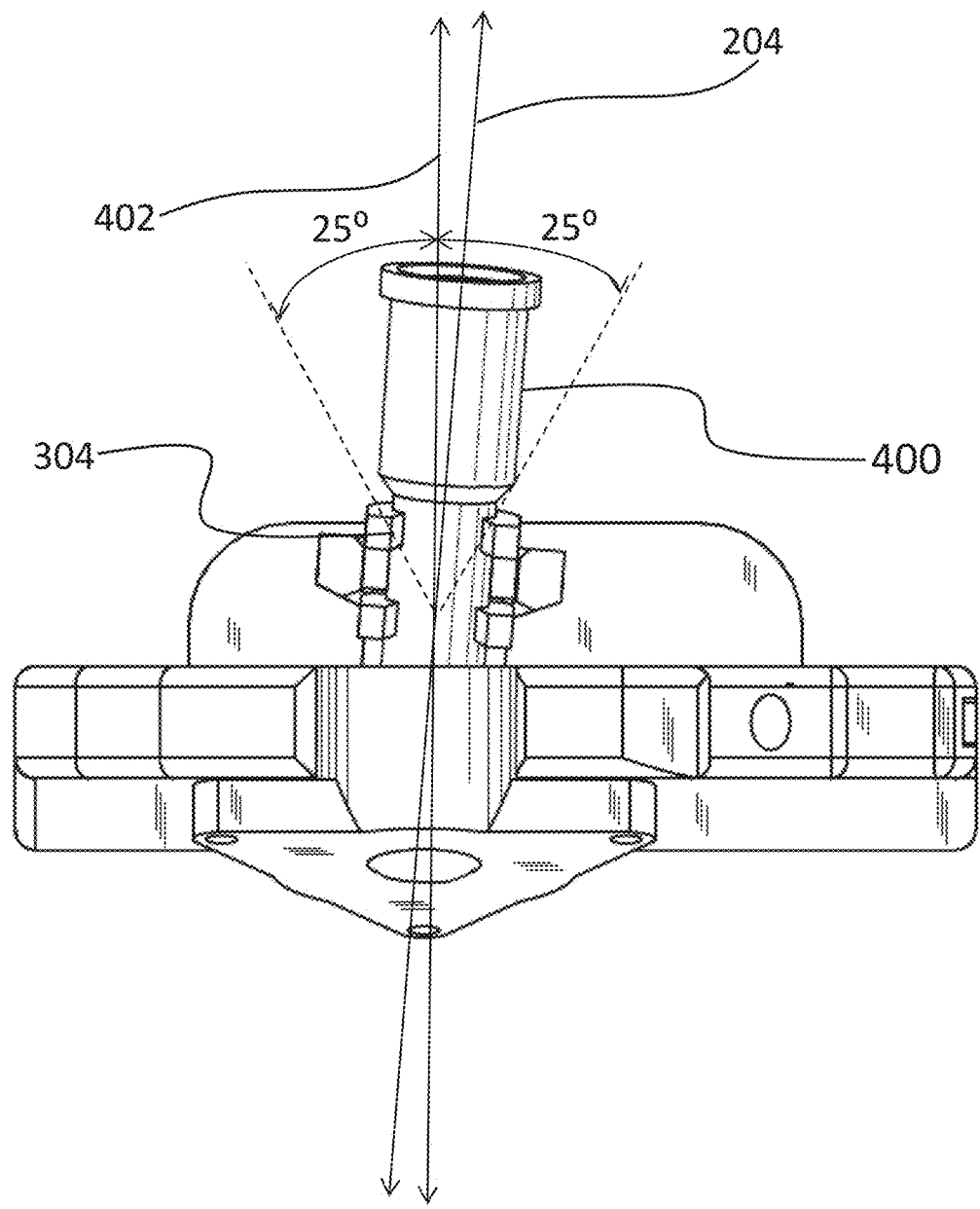
FIG. 4 is an elevational front edge view of the surgical trajectory alignment device of FIG. 1, showing a guide tube inserted within the receiving portion.

In use, the base 102 and the alignment trajectory guide holding portion 110 are operable for placement on a surface of the subject 200 (see FIG. 2). In order to couple the alignment trajectory guide holding portion 110 and the base 102 to the subject 200, in an embodiment, the alignment trajectory guide holding portion 110 defines at least one aperture 1500 (as illustrated in FIG. 15), operable to receive a screw or other fastener. In this embodiment, in order to couple the base 102 to the subject 200, the screw is inserted through the at least one aperture 1500 and screwed into the subject 200. In another embodiment, the alignment trajectory guide holding portion 110 and the base 102 may be removably coupled to the subject 200 using a burr hole and a screw, for example, when the subject 200 includes a human skull. In the embodiment of FIG. 14 and FIG. 15, the alignment trajectory guide holding portion 110 is operable to allow an operator to select a burr hole on the human skull. The burr hole configuration allows the operator to select an area on the subject 200 that may be least traumatic to the brain tissue, while aligning the medical device 104 with the target area 202. Advantageously, because the alignment trajectory guide holding portion 110 of FIG. 15 does not include the prior art locking ring 112, depicted in FIG. 14, which includes a diameter larger than a diameter of the locking ring 112 of FIG. 15, the presently inventive surgical trajectory alignment device 100 allows the operator to rotate the medical device 104 up to approximately 25° from a vertical axis 402, as best illustrated in FIG. 4. When the prior art locking ring 112 of the Navigus trajctory guide 1400 of FIG. 14 is used, the device 100 is only able to rotate the medical device 104 up to approximately 15° from the vertical axis 402. In other embodiments, the alignment trajectory guide holding portion 110 of FIG. 15 may be operable to rotate the medical device 104 a number of degrees outside of this range.

The presently inventive surgical trajectory alignment device 100 is envisioned for use with various types of medical procedures and on various subjects. In one embodiment, the subject 200 is a human. In an alternative embodiment, the subject may be, for example, an animal being operated on in a veterinary surgical procedure. The various embodiments of the presently inventive surgical trajectory alignment device, however, are not limited to any particular surgical procedure.

Figure 5:
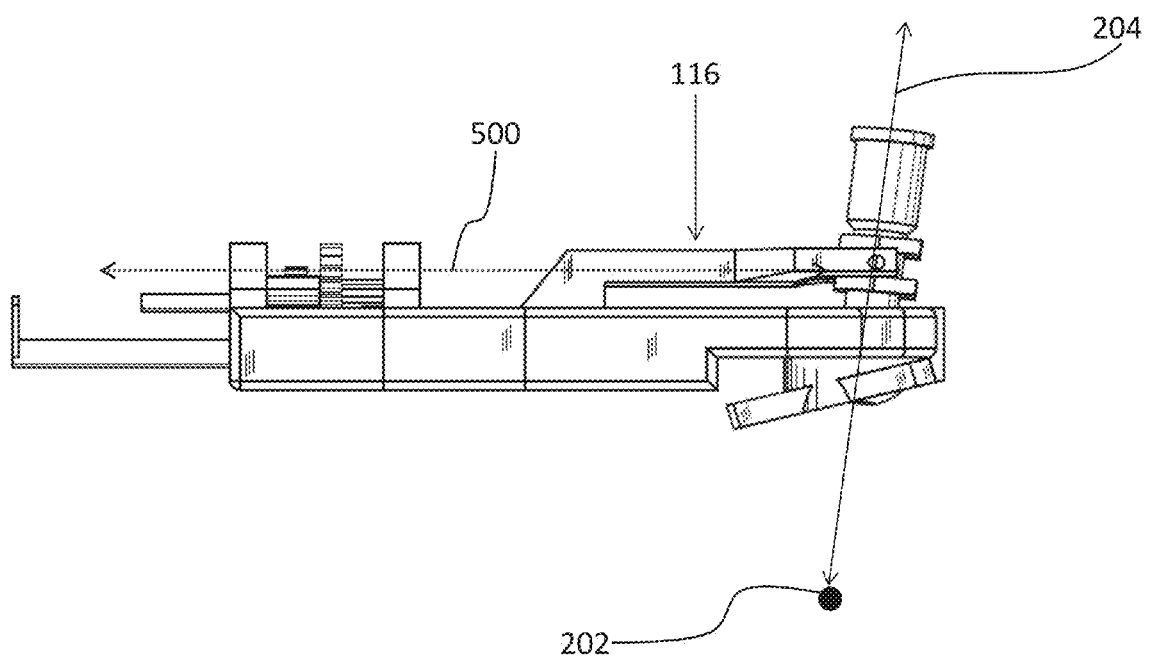
FIG. 5 is an elevational side view of the surgical trajectory alignment device of FIG. 1, showing an alignment axis.

Referring again to FIG. 2, an arm 116 is shown coupled to the base 102. The arm 116 is a device configured to align the medical device 104 to the target area 202 within the subject 200. The arm 116 is disposed in a horizontal position, substantially perpendicular to the entry axis 204 defined by the medical device 104. In use, the arm 116 is operable to align the medical device 104 to the target area 202 within the subject 200 by one of a rotational and a translational motion. The rotational motion is identified by element 120 in FIG. 1. The "rotational motion," as used herein, is intended to indicate movement in an arc motion 120 about an arm axis 122. The arc motion 120 provides adjustment of the medical device 104 about the vertical axis 402. The translational motion is identified by element 124 in FIG. 1. The "translational motion," as used herein, is intended to indicate movement along a linear path, e.g. a horizontal axis. Advantageously, this motion provides an operator with a simple configuration for performing trajectory alignment of the medical device 104 with the entry axis 204 (as illustrated in FIG. 5) to the target area 202, because the operator need only choose to perform at least one of the rotational and translation motion using the arm 116.

Figure 6:
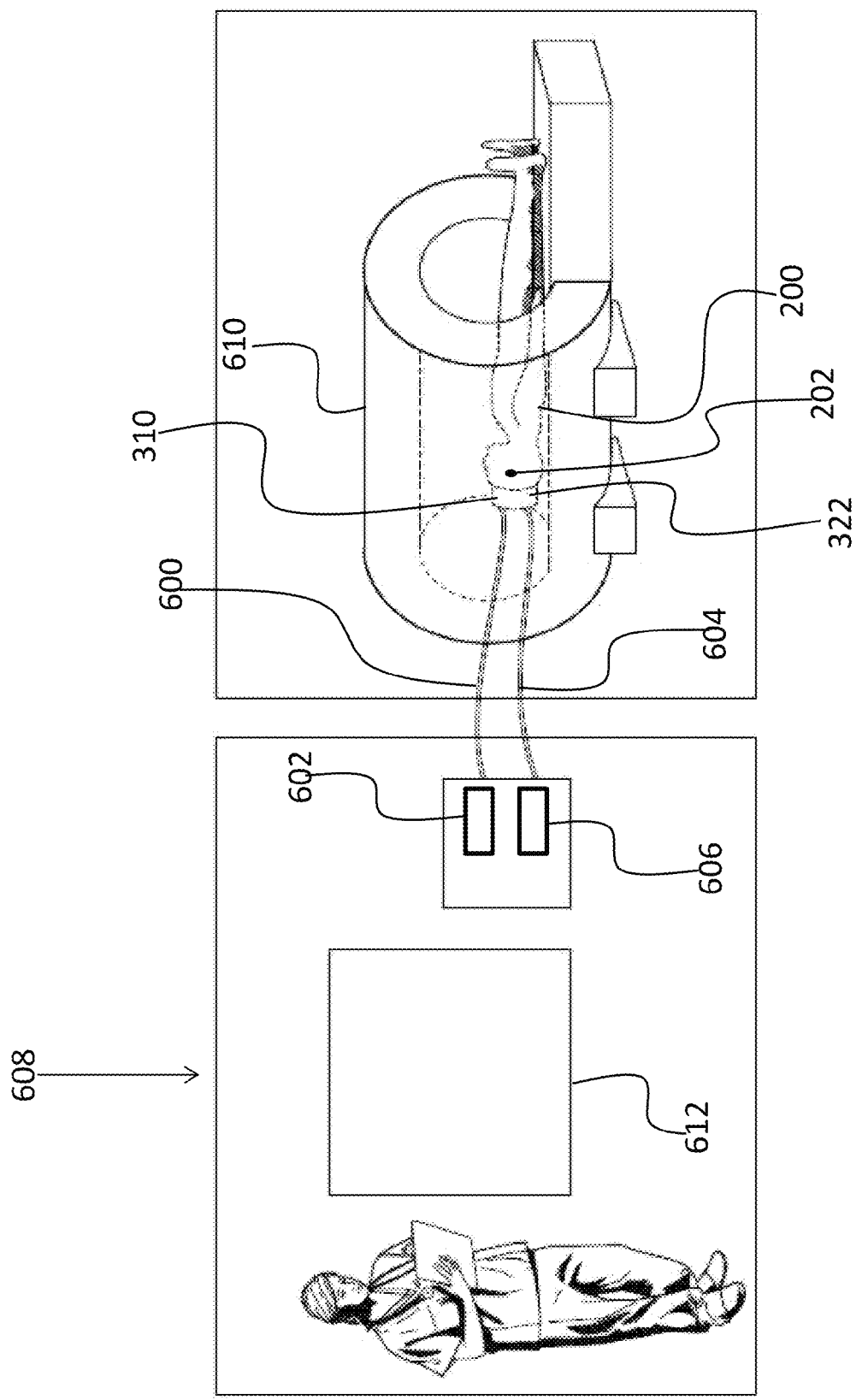
FIG. 6 is a block diagram representing an exemplary implementation of the surgical trajectory alignment device of FIG. 1 being used on a patient within an MRI system.

In an embodiment, the base 102 and the arm 116 are at least one of a plastic and a ceramic material. Advantageously, this material is compatible with a medical imaging scanner 610 (as illustrated in FIG. 6), such as an MRI scanner, so that the subject 200 can remain within the medical imaging scanner 610 during the manipulation of the surgical trajectory alignment device 100. Because the subject 200 does not have to be removed from the medical imaging scanner 610 to perform the trajectory alignment, the overall time for performing the trajectory alignment is reduced, thereby decreasing the labor costs in performing the medical procedure.

Figure 3:
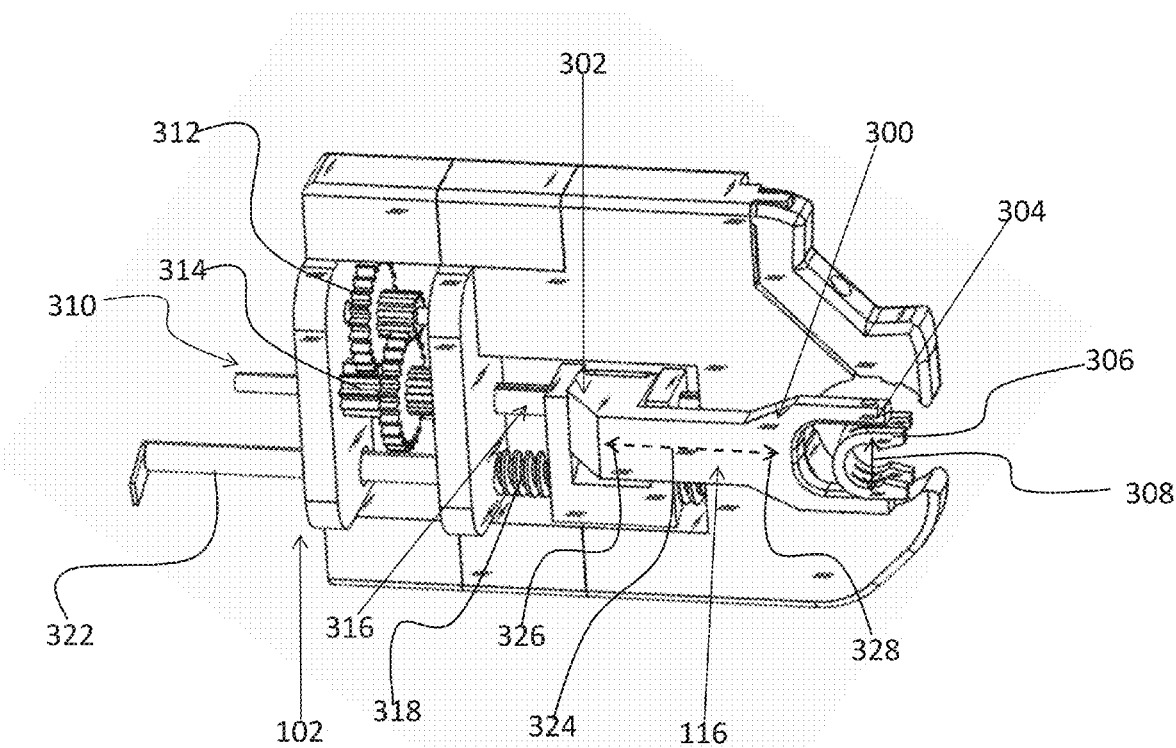
FIG. 3 is a perspective view of the top portion of the surgical trajectory alignment device of FIG. 1, showing an arm with a receiving portion, the arm being coupled to a rotation device and a translation device.

Now referring to FIG. 3, the arm 116 can be seen having a first end 300 and a second end 302, opposite the first end 300. The first end 300 has a receiving portion 304 shaped to receive and secure at least a portion of the medical device 104 (see FIG. 1). In an embodiment, the receiving portion 304 does not directly receive the medical device 104, rather, the receiving portion 304 is operable to receive a guide tube 400 (as illustrated in FIG. 4) for insertion of the medical device 104 within the guide tube 400. In another embodiment, the receiving portion 304 may directly receive the medical device 104. The guide tube 400 is a housing for securing the medical device 104 therein. Advantageously, the guide tube 400 creates a barrier on all sides of the medical device 104 to fix the medical device 104 in a stationary position.

The receiving portion 304 is shown having at least one finger 306, wherein the at least one finger 306 forms the opening 308 for receiving the guide tube 400. In another embodiment, the receiving portion 304 may include a plurality of fingers 306, operable to receive and secure the guide tube 400. In another embodiment, the receiving portion 304 may include a plurality of fingers 306, operable to receive and secure the medical device 104. The opening 308 defines a u-shaped cavity sized to accommodate the medical device 104. In one embodiment, the opening 308 is sized to accommodate a catheter having a circumference between approximately 0.1572 inches-0.3406 inches. In other embodiments, the receiving portion 304 may be shaped to receive and secure the medical device 104 having a circumference outside of these ranges. In another embodiment, the receiving portion 304 may define a round cavity, though the u-shaped cavity is preferred.

To accomplish the rotational motion, in an embodiment, a rotation device 310 is coupled to at least one gear and the at least one gear is coupled to the arm 116. In another embodiment, the rotation device 310 may be coupled to a single gear and the single gear may be coupled to the arm 116. In the embodiment of FIG. 3, the rotation device 310 is shown coupled to a first gear 312 and a second gear 314. The gears 312, 314 are shown coupled to a rod 316, wherein the rod 316 is coupled to the arm 116 at the second end 302. The gears 312, 314 are shown as rotationally coupled, such that, in use, the rotation device 310 rotates and causes the first gear 312 to rotate, which causes the second gear 314 to rotate. The gears 312, 314 are coupled to the rod 316, such that, as the gears 312, 314 rotate, the rod 316 is operable to rotate the arm 116 at the second end 302, to accomplish the rotational motion.

Referring now primarily to FIGS. 3 and 6, the gears 312, 314 advantageously provide an operator with a precise and predictable ratio between the rotational motion and the operator's movements at a second actuator 606. The rotational device 310 is shown in FIG. 6 coupled to the first actuator 602 by a first cable 600. In an embodiment, the first actuator 602 may include a knob for controlling the rotational device 310 from a remote control station 608. The operator may choose, for example, to turn the knob two degrees from the first actuator 602 which may result in rotating the arm 116 two degrees to rotate the medical device 104 two degrees about the vertical axis 402, illustrating a predictable correlation between the control input from the operator and the rotational, output motion of the medical device 104. This example is provided for illustrative purposes only, and the ratio between the rotational motion of the medical device 104 and the control input from the operator may vary outside of these ranges. The gears 312, 314 are also advantageous, because, if the operator stops turning the knob, the gears 312, 314 are operable to provide traction and stop the rotational motion of the arm 116.

A translation device 322 is shown coupled to the arm 116 at the second end 302 to accomplish the translation motion. The translation device 322 is shown coupled to the arm 116 by a screw 318 inserted into the second end 302. In use, as the translation device 322 is turned, the screw 318 is operable to turn and propel the arm 116 in precise minor increments along a linear path 324 from a first point 326 to a second point 328 along an alignment axis 500 (FIG. 5). The "alignment axis," as used herein, is intended to indicate a horizontal axis defined by a longitudinal length of the arm 116. In another embodiment, the translation device 322 may be coupled to the arm 116 at the second end 302 by a rod, bolt, or other fastener, as appreciated by one of ordinary skill in the art.

To facilitate the simple and rapid setup of the surgical trajectory alignment device 100, the rotation device 310 and the translation device 322 are shown coupled to the base 102 on a single side of the base 102. The operator, physician, or other medical personnel, can focus on coupling the first cable 600 and the second cable 604 (both shown in FIG. 6) to the single side of the base 102.

In accordance with an embodiment of the present invention, the first cable 600 is shown coupling the rotation device 310 to a first actuator 602. Likewise, the second cable 604 is shown coupling the translation device 322 to a second actuator 606. In the embodiment of FIG. 6, the cables 600, 604 are shown as electrical cables. In other embodiments, the cables 600, 604 may be mechanical cables, fiber optic cables, or a similar type of connection mechanism. The embodiment showing the cables 600, 604 as electric cables is preferred due to reduced friction when compared to using other types of cables 600, 604. The "actuator" is defined herein as a device that is operable to allow an operator to initiate movement of at least one of a rotation device and a translation device. In FIG. 6, the actuators 602, 606 are shown as electrical actuators. In another embodiment, the actuators 602, 606 may be mechanical actuators operable to convert rotary motion to linear motion.

In one embodiment, the actuators 602, 606 may be in the form of a pair of knobs provided on a distal end of the cables 600, 604 located in the room with the medical imaging display 612. The first actuator 602 and the second actuator 606 are shown at a remote control station 608 outside of the magnetic field of a magnetic imaging scanner 610, such as the MRI scanning device. The remote control station 608 is essentially the room where the medical imaging display 612 is located, and which is separate from the room where the medical imaging scanner 610 and the subject 200 are located. From the remote control station 608, the operator can view the medical imaging system, and manipulate the actuators 602, 606 to move at least one of the rotation device 310 and the translation device 322, which, in turn, perform at least one of the rotational and the translation motion, to align the medical device 104 (FIG. 1) with the target area 202 within the subject 200. Advantageously, the operator can rapidly perform the trajectory alignment because he or she only has to focus on performing at least one of the rotational motion and the translation motion to align the medical device 104 in a precise manner.

Figure 7:
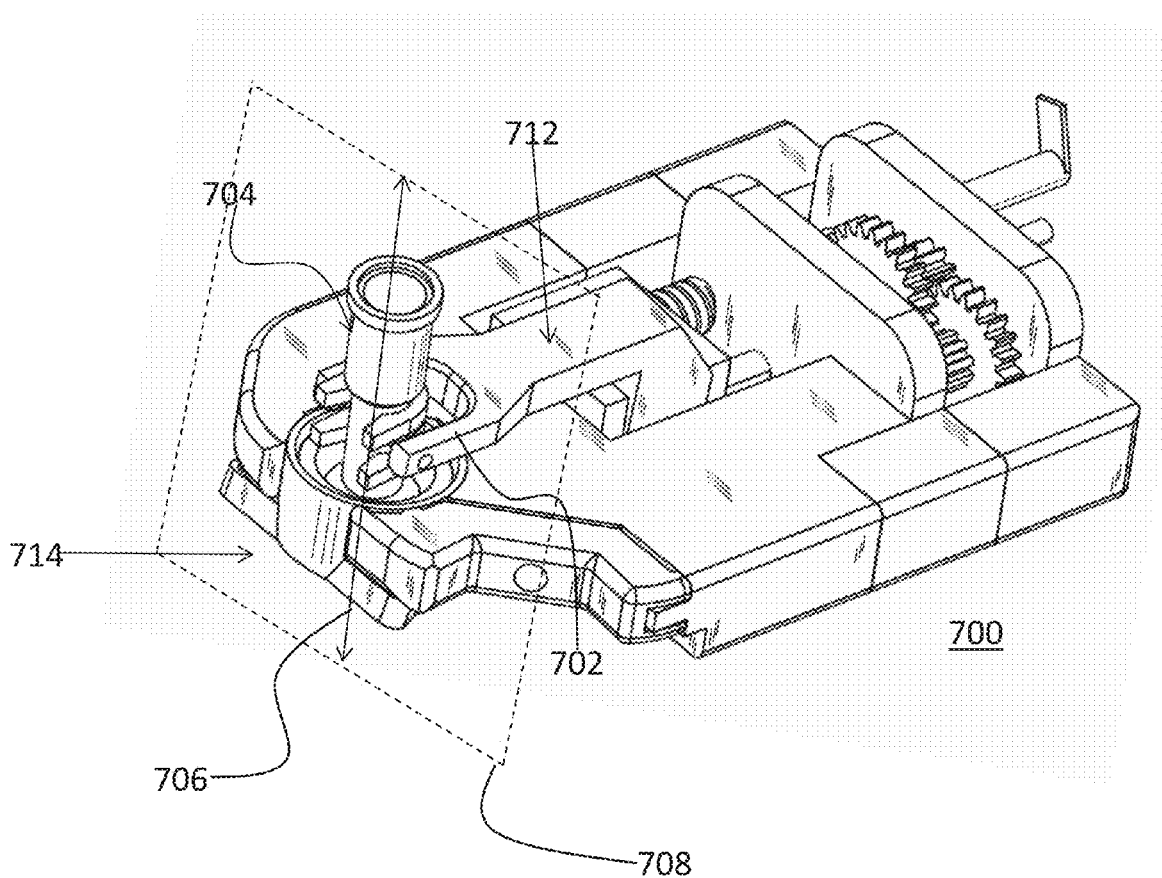
FIG. 7 is a perspective view of the top portion of an embodiment of the surgical trajectory alignment device in accordance with the present invention.
Figure 16:
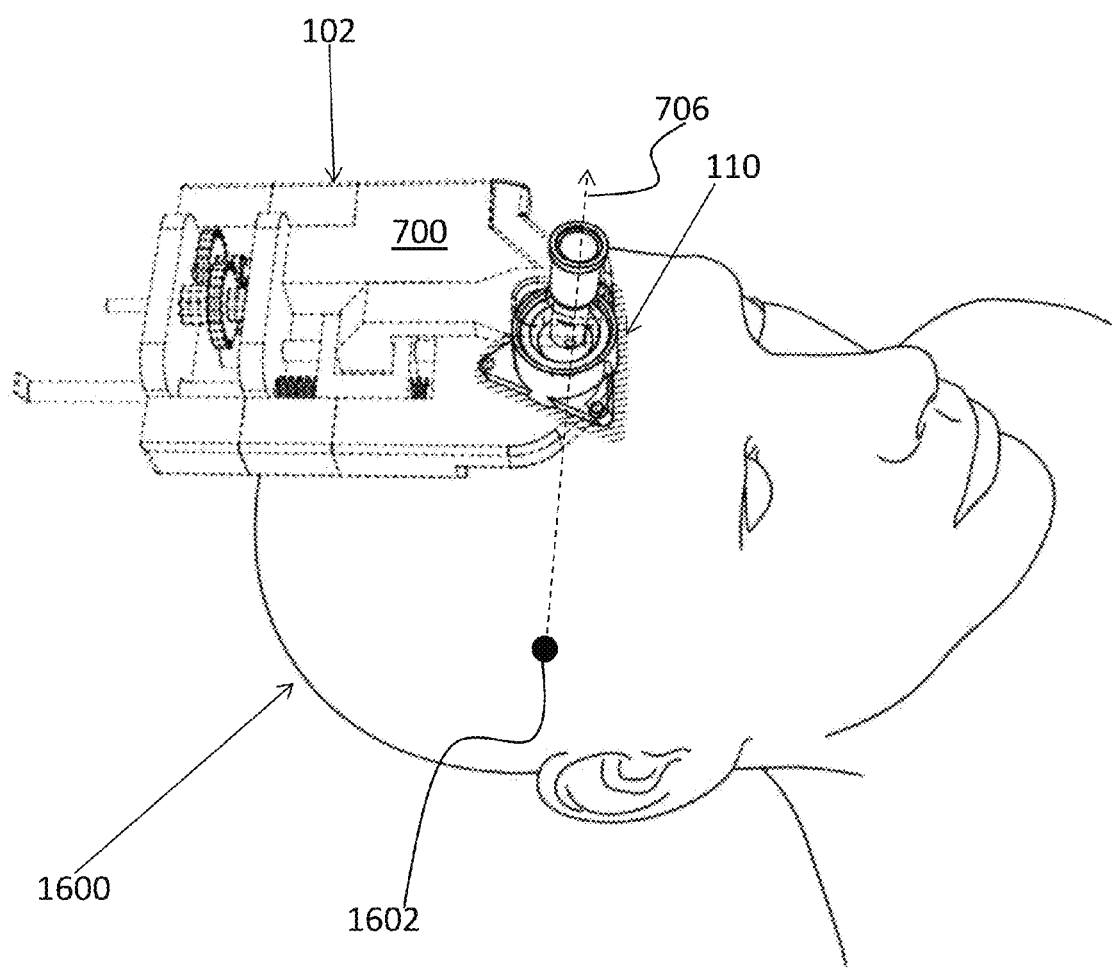
FIG. 16 is a downward-looking perspective view of the surgical trajectory alignment device of FIG. 7, showing the surgical trajectory alignment device removably coupled to the locking ring wherein the locking ring is removably coupled to a patient.

FIG. 7 illustrates a surgical trajectory alignment device 700 showing an alignment arm 712, substantially identical to the alignment arm 116 illustrated in FIG. 1, except described with reference to a plane 708 defined by a longitudinal patient entry axis 706 and a horizontal plane extending across a width of an alignment arm holding portion 702. The surgical trajectory alignment device 700 includes an alignment trajectory guide holding portion 714 and an alignment arm holding portion 702. The alignment trajectory guide holding portion 714 is shaped to receive and secure an alignment trajectory guide 704 along the longitudinal patient entry axis 706 falling within the plane 708. With reference primarily to FIG. 7 and FIG. 16, the "longitudinal patient entry axis" 706 is defined herein as an axis of a trajectory between the target area 202 within the subject 1600 and an entry point 914 on the subject 1600, through which the medical device 104 must enter the subject 1600 to reach the target area 202. This longitudinal patient entry axis 706, as illustrated in FIG. 7, lies with the plane 708. The alignment trajectory guide 704, similar to the guide tube 400, is configured to receive and support the medical device 104 (FIG. 1) for use during the surgical procedure. The alignment arm 712 is shown supporting the alignment trajectory guide holding portion 714.

Figure 8:
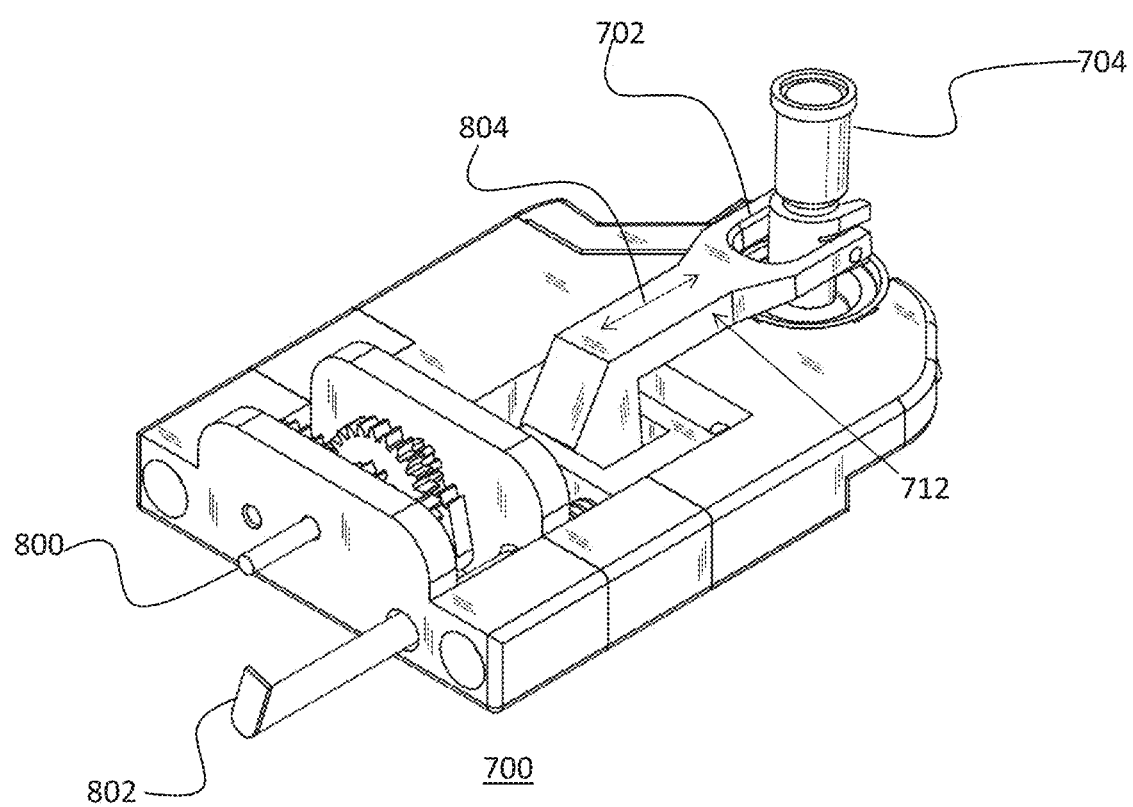
FIG. 8 is a perspective rear view of the surgical trajectory alignment device of FIG. 7, showing a first alignment trajectory guide holding portion activator and a second alignment trajectory guide holding portion activator.

Similar to the rotational device 310 of FIG. 3, FIG. 8 illustrates the surgical trajectory alignment device 700 having a first alignment trajectory guide holding portion activator 800. The first alignment trajectory guide holding portion activator 800 is operable to rotate the alignment trajectory guide 704 secured by the alignment arm holding portion 702 within the plane 708. Likewise, a second alignment trajectory guide holding portion activator 802 is shown. The second alignment trajectory guide holding portion activator 802 is operable to translate the alignment trajectory guide 704 secured by the alignment arm holding portion 702 in a direction away from the plane 708. The first alignment trajectory guide holding portion activator 800 and the second alignment trajectory guide holding portion activator 802 are shown as coupled to and operable to manipulate the alignment arm 712. The alignment arm 712 defines an arm axis 804, which is similar to the alignment axis 500 of FIG. 5. The "arm axis" is defined herein as a horizontal axis defined by a longitudinal length of the alignment arm 712.

Figure 9:
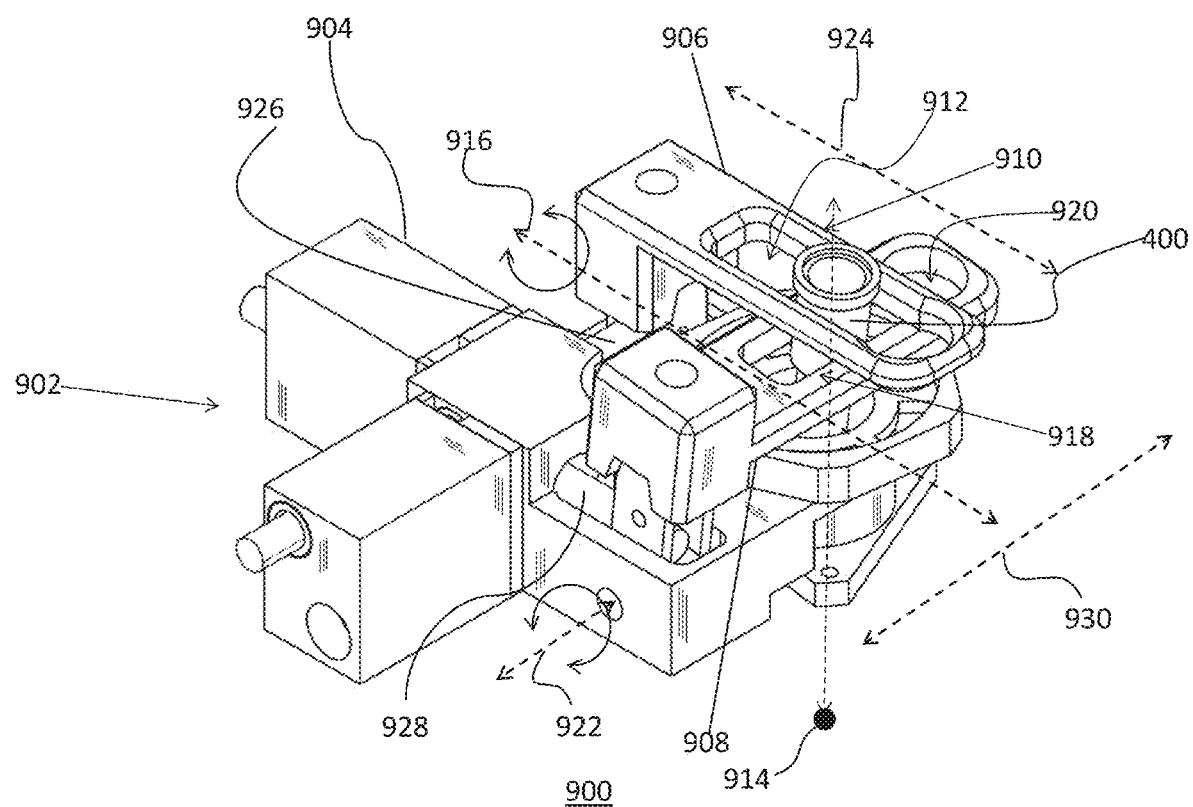
FIG. 9 is a perspective view of an exemplary embodiment of a surgical trajectory alignment device in accordance with the present invention showing a base having a first arm and a second arm.

FIG. 9 provides another illustrated embodiment of the present invention, showing a surgical trajectory alignment device 900 utilizing two arms, as opposed to one arm, as with the embodiments of FIG. 1 and FIG. 7. FIG. 9 illustrates a body 902 having a base 904 with a first arm 906 and a second arm 908. Another difference between the embodiment of FIG. 9 and the embodiments of FIG. 1 and FIG. 7, is that the first arm 906 and the second arm 908 are operably configured to align the entry axis 204 to the target area 202 (FIG. 2) by rotational movements, as opposed to both rotational and the translational movements illustrated in the embodiment of FIG. 1 and FIG. 7. The base 904 is removably couplable to the subject 1600, in the same or a similar manner as that described in reference to the embodiments of FIGS. 1 and 7. In one embodiment, the body 902 is comprised of a non-metallic material, such as a polymer material. In another embodiment, the material may be another type of non-metallic material, as would be appreciated by one of ordinary skill in the art. In yet another embodiment, the body 902 includes a metallic material, such as silver, copper and gold. Advantageously, the non-metallic material is compatible with the MRI scanner, so that the surgical trajectory alignment device 900 does not have to be removed from the subject 200 when the subject is placed within the MRI scanner.

The first arm 906 is shown in this embodiment coupled to the base 902 by a first rod 926. In another embodiment, the first arm 906 may be coupled to the base 902 by a bolt, screw, or other fastener. The first arm 906 has a receiving end 910 defining a first opening 912. FIG. 9 shows the first opening 912 having at least a portion of the guide tube 400 inserted therethrough. In another embodiment, the first opening 912 is operable for receiving at least a portion of the medical device 104 therethrough, for insertion of the medical device 104 (FIG. 1) through an entry point 914 on the subject 200 (FIG. 2). The "entry point" 914 is defined herein as an opening on the subject 200 through which the medical device 104 (FIG. 1) passes through in order to reach the target area 202 within the subject 200.

The first arm 906 is operably configured to rotate about a first axis 916. "Rotate" is defined herein as movement in an arc motion. The first axis 916 is shown substantially parallel to a longitudinal length 924 of the first arm 906. "Substantially parallel" is defined herein as having equal, or approximately equal, distances separating the two lines from each other in more than one point along the lines. "Longitudinal length" as used herein is intended to indicate a length extending along a longest direction of the respective arm 906, 908. The first axis 916 is operable for aligning the first arm 906 with the entry point 914 defined by target area 202 (FIG. 2).

The second arm 908 is shown coupled to the base 904 by a second rod 928. In another embodiment, the second arm 908 may be coupled to the base 904 by a bolt, a screw, or another fastener. The second arm 908 has a receiving end 918 defining a second opening 920. FIG. 9 shows the second opening 920 having at least a portion of the guide tube 400 inserted therethrough. The second opening 920 is operable for receiving at least a portion of the medical device 104 (FIG. 1) therethrough for insertion of the medical device 104 through the entry point 914 on the subject 200.

The second arm 908 is operably configured to rotate about a second axis 922 for aligning the entry axis 204 to the target area 202 within the subject 200 (FIG. 2). The second axis 922 can be seen as substantially parallel to a longitudinal length 930 of the second arm 908 and substantially perpendicular to the first axis 916. "Substantially perpendicular" is defined herein as forming a right angle, or approximately a right angle, with another line, plane, or surface.

The receiving end 910 of the first arm 906 is shown overlapping the receiving end 918 of the second arm 908. In use, this configuration facilitates jointly guiding movement of the medical device 104 to align with the target area 202. In other words, as the first arm 906 rotates about the first axis 916 and the second arm 908 rotates about the second axis 922, the medical device 104 is able to be moved about in a precise manner to align with the target area 202. Advantageously, this configuration provides a simple configuration for guiding the medical device 104 because the operator need only manipulate the first arm 906 and/or the second arm 908 in order to align the entry axis 204 to the target area 202 within the subject 200 (FIG. 2).

Figure 10:
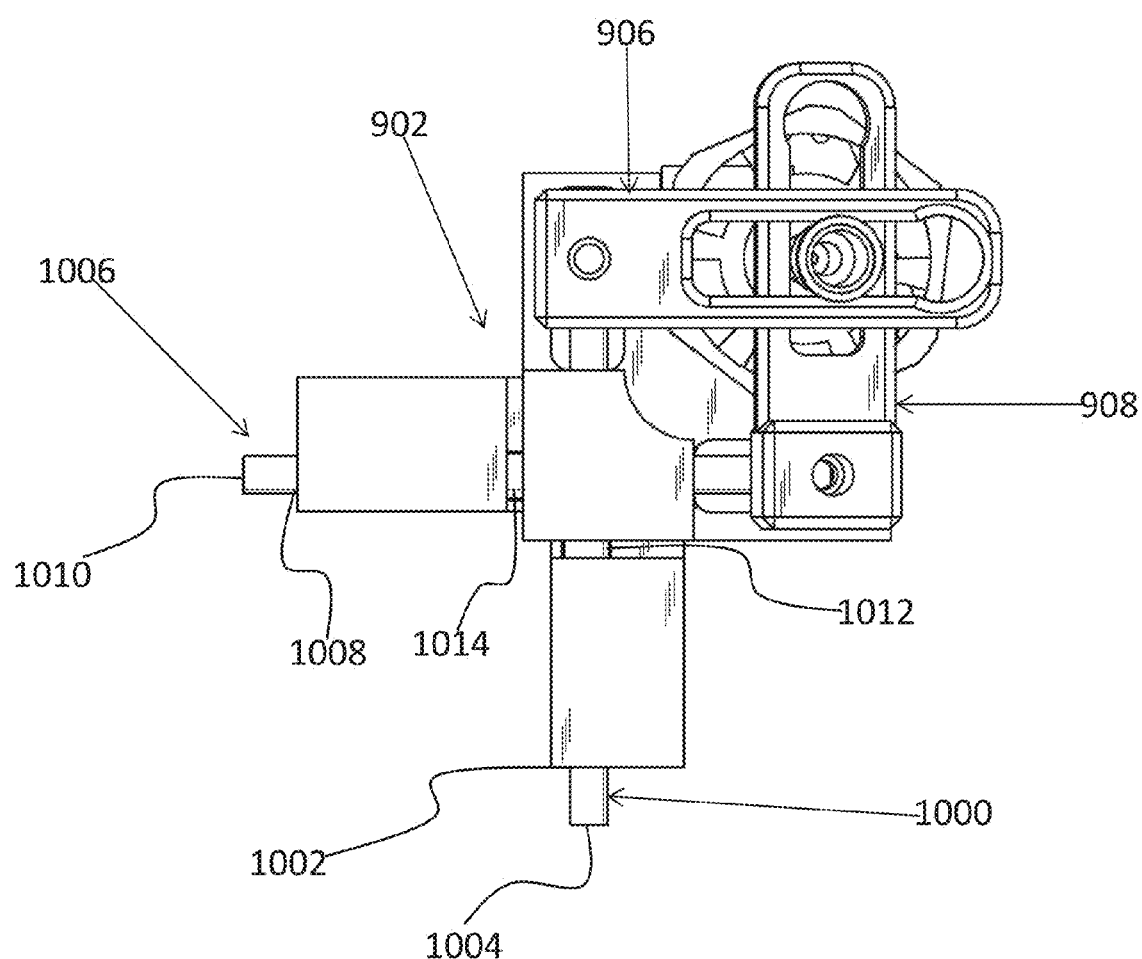
FIG. 10 is a top plan view of the surgical trajectory alignment device of FIG. 9, showing a first rotation device and a second rotation device.

Referring now primarily to FIG. 10, the body 902 is shown having a first rotation device 1000 and a second rotation device 1006 in order to accomplish the jointly guiding movement of the medical device 104. The first rotation device 1000 is shown having first end 1002 and a second end 1004. The first end 1002 is shown coupled to the first arm 906 by a first shaft 1012. The first shaft 1012 is operable to rotate the first arm 906. In another embodiment, the first end 1002 may be coupled to the first arm 906 by a screw or other fastener. In another embodiment, the first end 1002 may be coupled to the first arm 906 by a gear, operable to rotate the first arm 906, similar to the gear configuration described in reference to FIG. 3.

A second rotation device 1006 is shown couple to the second arm 908. The second rotation device 1006 is shown having a first end 1008 and a second end 1010. The first end 1008 is shown coupled to the second arm 908 by a second shaft 1014. The first shaft 1012 is operable to rotate the first arm 906. In another embodiment, the first end 1008 may be coupled to the second arm 908 by a screw or other fastener. In another embodiment, the first end 1008 may be coupled to the second arm 908 by a gear, operable to rotate the second arm 908, similar to the gear configuration described in reference to FIG. 3.

Referring now primarily to FIGS. 6 and 10, the second end 1004 may be coupled to the actuator 606 at the remote control station 608 by the first cable 600. In another embodiment, the second end 1004 may be coupled to the actuator 606 at the remote control station 608 by an electrical wire, or another similar connection mechanism. Similar to the second end 1004 of the first rotation device 1000, in an embodiment, the second end 1010 of the second rotation device 1006 may be coupled to the actuator 606 at the remote control station 608 by the second cable 604. The medical imaging display 612 is located within the remote control station 608. From the remote control station 608, the operator can view the medical imaging display 612, and manipulate the actuators 602, 606 to move the first rotation device 1000 and the second rotation device 1006, which in turn rotate the arms 906, 908 about the first axis 916 and the second axis 922, respectively, to align the medical device 104 with the target area 202 within the subject 200.

Figure 11:
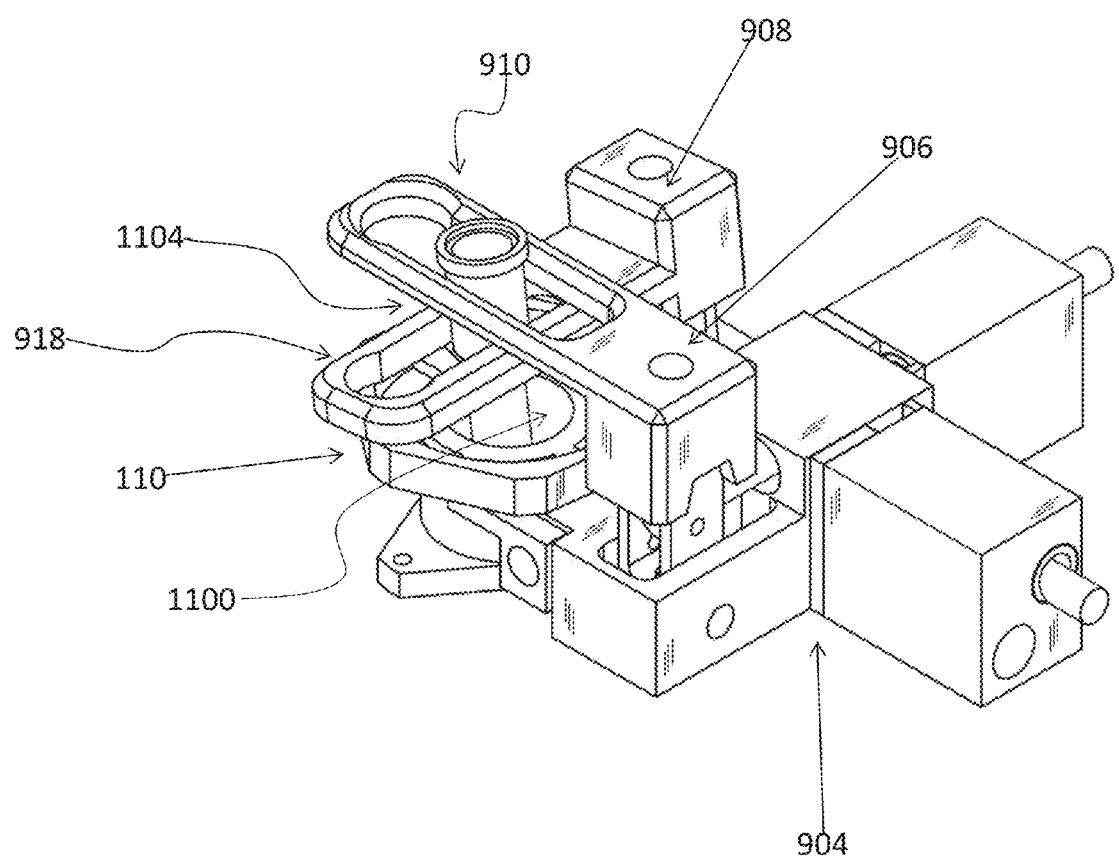
FIG. 11 is a perspective view of the surgical trajectory alignment device of FIG. 9, showing an opening for receiving an alignment trajectory guide holding portion, the opening disposed below the first and the second arm.

FIG. 11 shows that the base 904 defines a third opening 1100 operably configured to receive the alignment trajectory guide holding portion 110. FIG. 11 shows the third opening 1100 disposed below an intersection area 1104 defined by the region where the receiving end 910 of the first arm 906 overlaps the receiving end 918 of the second arm 908.

Figure 12:
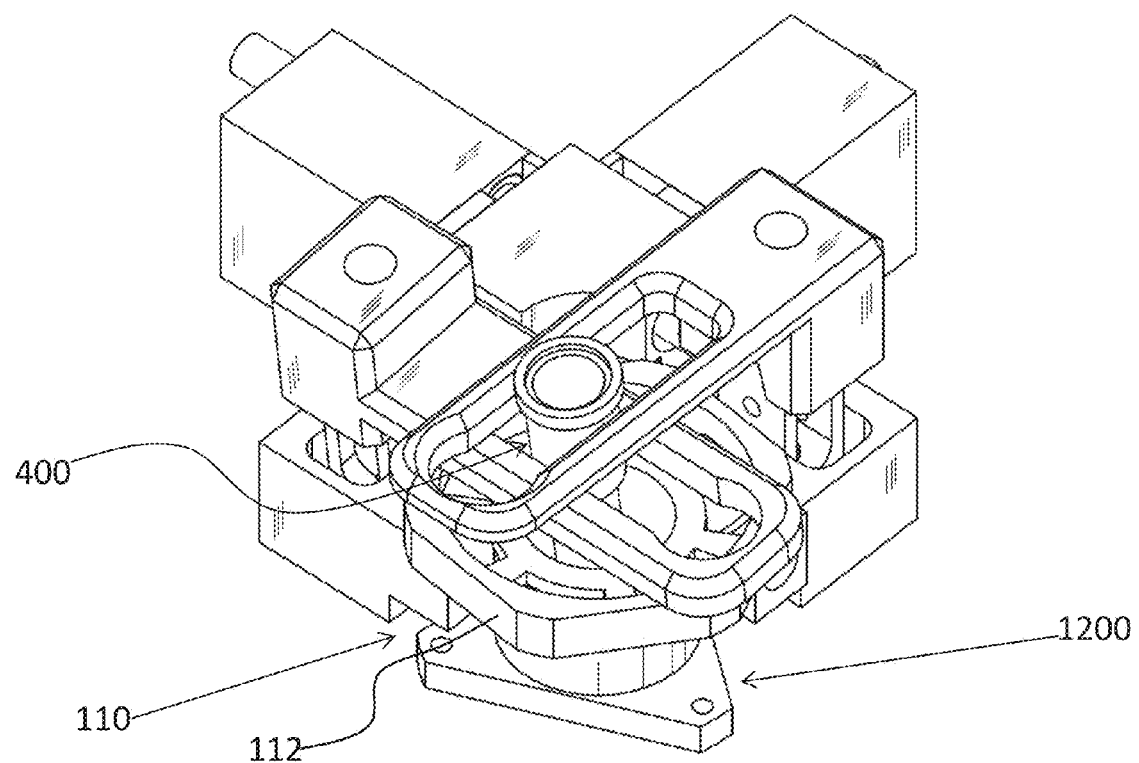
FIG. 12 is a perspective rear view of the surgical trajectory alignment device of FIG. 9, showing a base member coupled to a locking ring.
Figure 13:
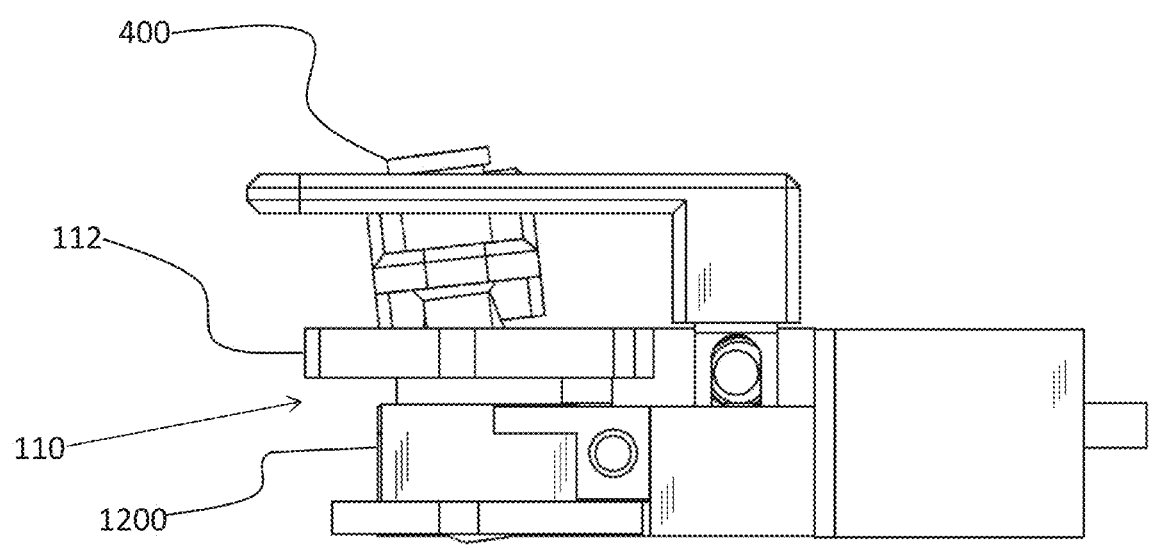
FIG. 13 is an elevational side view of the surgical trajectory alignment device of FIG. 9, showing the base member coupled to the locking ring.

FIGS. 12 and 13 show the alignment trajectory guide holding portion 110 having a base member 1200 coupled to the locking ring 112. The alignment trajectory guide holding portion 110 may include a ball joint configuration that provides rotary movement of the medical device 104 in all directions through the movement of the guide tube 400 within the locking ring 112.

FIGS. 14 and 15 illustrate various embodiments of the alignment trajectory guide holding portion 110. In FIG. 14, the exemplary implementation of the alignment trajectory guide holding portion 110 is utilized with a locking ring 112 from the Navigus trajectory guide 1400 as manufactured by Medtronic®. Advantageously, the presently inventive surgical trajectory alignment device 100, 700, 900 is operable to couple to different embodiments of the alignment trajectory guide holding portion 110. The surgical trajectory alignment device 100, 700, 900 may be coupled to pre-existing Navigus trajectory guides 1400 for access to a wider, more accurate range of motion during trajectory alignment. In an embodiment, the Navigus trajectory guide 1400 is operable to adjust the guide tube 400 and the medical device 104 (FIG. 1) by at least 15° from the vertical axis. In another embodiment, the Navigus trajectory guide 1400 may be operable to adjust the guide tube 400 within a range of degrees outside of this range.

FIG. 15 shows the preferred embodiment of the alignment trajectory guide holding portion 110 operable to securely hold the guide tube 400 in place. The locking ring 112 is shown as an annular ring having a diameter 1502 less than a diameter 1504 of the base member 1200, and less than a diameter 1402 of the locking ring 112 depicted in FIG. 14. The locking ring 112 is sized to be received through a top opening 1202 of the base member 1200. In other words, the locking ring 112 is sized to fit within the base member 1200. Advantageously, this size allows the locking ring 112 to be frictionally retained within the base member 1200. "Frictionally retained" is defined herein as tightly held in place. Additionally, providing the locking ring 112 with the diameter 1502 less than the diameter 1504 of the base member 1200 is advantageous because the smaller diameter facilitates rotation of the guide tube 400 and the medical device 104 by approximately 25° from the vertical axis 402 (FIG. 4). In contrast, the wider locking ring 112 depicted in FIG. 14, allows rotation by approximately 15° from the vertical axis 402. Accordingly, the locking ring 112 of FIG. 15 provides a wider range of motion for the trajectory of the medical device 104. In other embodiments, the diameter 1502 may be operable to facilitate adjustment of the guide tube 400 and the medical device 104 by a number of degrees outside of these ranges.

FIG. 16 shows the alignment trajectory guide holding portion 110 coupled to the subject 1600. In this embodiment, the base 102 is shown removably coupled to the alignment trajectory guide holding portion 110.

A surgical trajectory alignment device has been disclosed that is operable for aligning an instrument with a designated area, in a precise and rapid manner. Embodiments of the invention disclose a surgical targeting alignment device that is simple to assemble, use, and manufacture, and which is operable for guiding a medical device to a target area within a subject through an entry point on the subject, utilizing dual-arm rotational motion and without requiring the physician to be at the MRI scanner. In addition, embodiments of the invention have been disclosed that provide a surgical trajectory alignment device that utilizes both rotational and translational motion of a singular alignment arm to align the medical device to the target area.

What is claimed is:

1. A surgical trajectory alignment device comprising:
   an alignment trajectory guide holding portion shaped to receive and secure an alignment trajectory guide along a longitudinal patient entry axis, the longitudinal patient entry axis falling within a plane;
   a first alignment trajectory guide holding portion activator operable to rotate the alignment trajectory guide within the plane; and
   a second alignment trajectory guide holding portion activator operable to translate the alignment trajectory guide in a direction away from the plane, wherein the alignment trajectory guide is secured by an alignment arm holding portion.

2. The surgical trajectory alignment device according to claim 1, further comprising:
   an alignment arm supporting the alignment trajectory guide holding portion.

3. The surgical trajectory alignment device according to claim 2, wherein:
   the first alignment trajectory guide holding portion activator and the second alignment trajectory guide holding portion activator are coupled to and manipulate the alignment arm.

4. The surgical trajectory alignment device according to claim 2, wherein:
   the alignment arm defines an arm axis; and
   the direction away from the plane is a longitudinal direction of the arm axis.

5. A surgical trajectory alignment device for guiding a medical device to a target area within a subject through an entry point on the subject, the surgical trajectory alignment device comprising:
   a base couplable to a subject;
   a medical device extending through the base and into the subject; and
   an arm coupled to the base, the arm:
      having a receiving portion shaped to receive and secure at least a portion of the medical device;
      operably configured to rotate the medical device through the base and upon an alignment axis for aligning the medical device with a target area within the subject; and
      operably configured to translate the medical device through the base and along the alignment axis for aligning the medical device with the target area within the subject
   a rotation device coupled to the arm and operable to rotate the arm about the alignment axis; and
   a translation device coupled to the arm and operable to translate the arm along a linear path from a first point to a second point along the alignment axis.

6. The surgical trajectory alignment device according to claim 5, wherein:
   the base defines an opening operably configured to receive an alignment trajectory guide holding portion shaped to receive and secure an alignment trajectory guide.

7. The surgical trajectory alignment device according to claim 5, further comprising:
   a first cable coupling the rotation device to a first actuator located at a remote control station outside a magnetic field of a magnetic resonance imaging device.

8. The surgical trajectory alignment device according to claim 5, further comprising:
   at least one gear coupled to the rotation device.

9. The surgical trajectory alignment device according to claim 5, wherein:
the rotation device and the translation device are on a single side of the base.

10. The surgical trajectory alignment device according to claim 5, wherein:
the arm is configured to align the medical device to the target area within the subject by one of a rotational and a translational motion.

11. The surgical trajectory alignment device according to claim 5, wherein:
the arm:
includes a first end and a second end, opposite the first end;
includes at least one finger at the first end, the finger forming an opening for receiving the medical device therethrough and the finger operably configured to receive a portion of a guide tube, the guide tube configured to receive the medical device; and
coupled to a rotation device at the second end.

12. The surgical trajectory alignment device according to claim 5, wherein:
the arm is disposed in a horizontal position, substantially perpendicular to the entry point defined by the medical device.

13. The surgical trajectory alignment device according to claim 5, wherein:
the base and the arm are of at least one of a plastic and a ceramic material.

14. A surgical trajectory alignment device for guiding a medical device to a target area within a subject through an entry point on the subject, the surgical trajectory alignment device comprising:
a body including:
a base having a portion couplable to a subject;
a first arm:
coupled to the base;
having a receiving end defining a first opening for receiving at least a portion of the medical device therethrough for insertion of the medical device through an entry point on the subject;
operably configured to rotate about a first axis substantially parallel to a longitudinal length of the first arm for aligning an entry axis defined by the medical device to a target area with the subject;
a second arm:
coupled to the base;
having a receiving end defining a second opening for receiving at least a portion of the medical device therethrough for insertion of the medical device through the entry point on the subject;
operably configured to rotate about a second axis for aligning the entry axis to the target area with the subject, the second axis:
substantially parallel to a longitudinal length of the second arm, and
substantially perpendicular to the first axis,
wherein the receiving end of the first arm overlaps the receiving end of the second arm for jointly guiding movement of the medical device therein.

15. The surgical trajectory alignment device of claim 14, wherein:
the body further includes:
a first rotation device having a first end and a second end, the first end coupled to
the first arm, and the second end coupled to an actuator at a remote control station in close proximity to a medical imaging display;
a second rotation device having a first end and a second end, the first end coupled to the second arm, and the second end coupled to the actuator at a remote control station in close proximity to a medical imaging display.

16. The surgical trajectory alignment device of claim 14, wherein:
the first arm and the second arm are operably configured to align the entry axis to the target area by rotational movements.

17. The surgical trajectory alignment device of claim 14, wherein:
the body is comprised of a non-metallic material, the non-metallic material compatible with a Magnetic Resonance Imaging (MRI) scanner.

18. The surgical trajectory alignment device of claim 14, wherein:
the base defines a third opening operably configured to receive a base member of a NAVIGUS® trajectory guide, the opening disposed below an intersection area, the intersection area defined by the area where the receiving end of the first arm overlaps the receiving end of the second arm.

19. The surgical trajectory alignment device of claim 14, wherein:
the base defines a third opening for receiving a base member coupled to a locking ring, the locking ring:
including a diameter less than a diameter of the base member; and
sized to be received through a top opening of the base member and frictionally retained within the base member.

* * * * *